United States Patent
Carlsson et al.

(10) Patent No.: US 6,968,036 B2
(45) Date of Patent: *Nov. 22, 2005

(54) RADIATION THERAPY DEVICE

(75) Inventors: Per Carlsson, Sundbyberg (SE); Gert Hanner, Kalmar (SE); Ivars Alksnis, Trångsund (SE); Anders Nilsson, Stockholm (SE); Peter Fröberg, Vaxholm (SE)

(73) Assignee: Elekta AB, Stockholm (SE)

( * ) Notice: Subject to any disclaimer, the term of this patent is extended or adjusted under 35 U.S.C. 154(b) by 109 days.

This patent is subject to a terminal disclaimer.

(21) Appl. No.: 10/608,004

(22) Filed: Jun. 30, 2003

(65) Prior Publication Data
US 2004/0136495 A1 Jul. 15, 2004

(30) Foreign Application Priority Data
Jul. 5, 2002 (SE) .................................... 0202104

(51) Int. Cl.$^7$ ................................................ A61N 5/10
(52) U.S. Cl. ........................................................ 378/65
(58) Field of Search .............................. 378/65; 604/20

(56) References Cited

U.S. PATENT DOCUMENTS

| | | | |
|---|---|---|---|
| 4,739,173 A | 4/1988 | Blosser et al. | |
| 5,332,908 A | 7/1994 | Weidlich | |
| 5,528,653 A * | 6/1996 | Song et al. | .................. 378/65 |
| 5,757,886 A | 5/1998 | Song | |
| 6,041,101 A | 3/2000 | Kooy et al. | |
| 6,044,126 A | 3/2000 | Rousseau et al. | |
| 6,512,813 B1 * | 1/2003 | Krispel et al. | ................ 378/65 |
| 2004/0184577 A1 * | 9/2004 | Carlsson et al. | .............. 378/65 |

FOREIGN PATENT DOCUMENTS

| | | |
|---|---|---|
| DE | 101 40 100 | 3/2002 |
| EP | 1 057 499 | 12/2000 |
| SE | 517 625 | 8/1997 |

* cited by examiner

Primary Examiner—Edward J. Glick
Assistant Examiner—Thomas R. Artman
(74) Attorney, Agent, or Firm—Buchanan Ingersoll PC

(57) ABSTRACT

A radiation therapy device and a method of changing the spatial dose distribution surrounding a focus are disclosed. A subset of radioactive sources in a source carrier arrangement is displaceable relatively to collimator passage inlets, while the rest of the sources are fixed relatively to said collimator passage inlets.

30 Claims, 12 Drawing Sheets

RADIATION THERAPY DEVICE

TECHNICAL FIELD

The present invention relates to a radiation therapy device of the type comprising a source carrier arrangement carrying radioactive sources and a collimator body for directing radiation emanating from the sources toward a substantially common focus. The invention also relates to a method of changing the spatial dose distribution surrounding such a focus.

BACKGROUND OF THE INVENTION

The development of surgical techniques have made great progress over the years. For instance, patients who need to be operated in the brain, can nowadays undergo non-invasive surgery with very little trauma to the patient.

Leksell Gamma Knife® provides such surgery by means of gamma radiation. The radiation is emitted from fixed radioactive sources and are focused by means of collimators, i.e. passages or channels for obtaining a beam of limited cross section, toward a defined target. Each of the sources provide only a small dose to intervening tissue, with the resulting maximum radiation dose available only at the common focus where the radiation beams intersect. The target volume is determined, e.g. depending on the size of tumor to be radiated, by selecting different sizes of collimators. A type of collimator body called a "helmet", shaped like a hemisphere, is provided with collimators of one defined size which at the target area or a site of focus provides a certain radiation beam diameter. If another beam diameter is desired, the helmet must be changed to another helmet having a suitable size of collimators.

Even though the radiation therapy can be successfully carried out with the above described equipment, it may be desirable to reduce the time which lapses during the changing of helmets.

U.S. Pat. No. 5,757,886 discloses a medical radiating unit, in which a collimator carrier carries several sets of collimators of different aperture diameters distributed in correspondence with the distribution of radioactive sources in a source carrier. The collimator carrier and the source carrier may be rotated relative to each other, thereby enabling a change from one set of collimators to another set of collimators. This eliminates the need to use several helmets in order to be able to change collimator sizes. However, it is still quite limited as regards possibilities to choose different spatial dose distributions surrounding the focus. Another example is a whole-body radiotherapy device as disclosed in EP 1057499, which is also quite limited as regards variation of spatial dose distribution.

SUMMARY OF THE INVENTION

The object of the present invention is to provide a radiation therapy device and a method which alleviate the drawbacks of the prior art devices.

This is accomplished by a radiation therapy device and a method as defined in the accompanied claims.

The invention is based on the understanding that an abundance of variation as regards change of spatial dose distribution surrounding a focus is made possible by enabling some of the radioactive sources in a radiation therapy device to be displaceable at the same time as other radioactive sources in said device are kept still. The invention does not exclude the possibility of moving all the sources simultaneously, but on the contrary presents an option of moving a limited number out of the total number of sources, i.e. as an alternative to the traditional way of moving all the sources by e.g. moving an entire source body. The present invention provides several advantages, such as for instance a variety of different dose gradients, as will be described in the following.

Thus, according to one aspect of the invention a radiation therapy device is provided. It comprises a source carrier arrangement carrying radioactive sources. It also comprises a collimator body comprising collimator passages, suitably in the form of long and narrow through holes, for directing radiation emanating from said sources toward a substantially common focus. Each collimator passage has an inlet for receiving said radiation. The source carrier arrangement is arranged to allow for a subset of said sources to be displaced relatively to said collimator passage inlets, while the rest of said sources are fixed relatively to said inlets, thereby enabling a change of spatial dose distribution surrounding said focus.

Analogously to the above aspect of the invention, according to another aspect of the present invention a method of changing the spatial dose distribution surrounding the focus is provided. The method is characterized by displacing a subset of said sources relatively to said collimator passage inlets, while keeping the rest of the sources fixed relatively to said collimator passage inlets.

The source carrier arrangement may be designed in various ways which enable a subset of sources to be displaced while these sources, as well as the rest of the sources, are carried by the source carrying arrangement both before and after the displacement. Such a selective. displacement of sources during radiation therapy obviously provides many advantages.

According to at least one embodiment of the invention the source carrier arrangement comprises a number of segments, at least two or more, such as six or eight, or even as many as sixty. Each segment carries a subset of said sources and is individually displaceable. For practical reasons it is preferred to have the source carrier arrangement segmented as described. However, an alternative would be to provide the collimator body with individually movable segments, and another alternative would be to provide both the collimator body and the source carrier arrangement with individually movable segments. In the following, however, only a segmented source carrier arrangement will be discussed.

Since the segments are individually displaceable and controllable, it is e.g. possible to have one or more segments in register with inlets to collimator passages which direct toward the focus a radiation beam of a first cross-section or diameter, and simultaneously have one or more segments in register with inlets to collimator passages which give a beam of a second cross-section or diameter. Furthermore, one or more segments may be completely or partly shut off, i.e. all or some of the sources are arranged between or beside the collimator passage inlets. It should be noted that any two segments do not necessarily have to be displaceable in the same direction or parallel direction, but on the contrary each segment may be displaceable in its own linear direction.

One advantage of being able to shut off one or more segments, i.e. shielding the radiation sources in said segments, while keeping the rest active, is that the dose gradient from that direction is thereby altered. Thus, it is possible to only radiate from a certain direction, thereby avoiding e.g. some critical structures in the patient's body to be unnecessarily exposed.

The sources are arranged in a pattern on the source carrier arrangement, said pattern preferably corresponding to a pattern of at least one group or set of collimator passage inlets. Thus, the sources may be arranged in register with said set of collimator passage inlets so as to provide a desired spatial dose distribution, or they may be removed from that set of collimators to a complete shut-off position when none of the sources are in register with the collimator passage inlets. The displacement of a segment may even be made so that only some of the sources in said segment are in register with said inlets, while the other sources are shut off.

The collimator body may be provided with several groups or sets of collimator passages, each set being designed to provide a radiation beam of a respective specified cross-section or diameter toward the focus. Suitably, the inlets of each set of collimator passage has a pattern that essentially corresponds to the pattern of the sources on the source carrier arrangement. These sets of collimator passage inlets may be arranged so that when a subset of sources is displaced it is possible to change from one set of collimator passage inlets to another, thereby changing the resulting beam diameters and the spatial dose distribution surrounding the focus. The number of sets of collimator passages with different cross-sections or diameter may be more than two, such as three or four, or even more.

The sets of collimator passage inlets may be arranged in the collimator body in various ways. For instance, each set may comprise a specific size of collimator passage arranged in a cluster and thus separately from the other sets. Alternatively, the collimator passage inlets of one set may be arranged in a scattered relationship with collimator passage inlets of the other sets. This second alternative, may for instance be implemented in the following way. Each set of collimator passage inlets comprises a number of rows of collimator passage inlets. For instance, if three sets are provided in the collimator body, a row from a first set may have a row from a second set as its neighbour, said second set having a following row from a third set as a neighbour, which is followed by a row from the first set again. This alternating pattern means that the sources are suitably also arranged in a corresponding pattern of rows, the distance between two neighbouring rows of sources being equal to the distance between two spaced apart rows of collimator passage inlets from the same set. Thus, the distance between the rows of sources will in this case be about three times the distance between two consecutive rows of collimator passage inlets (having different passage cross-sections or diameters).

It is to be understood that a row of collimator inlets does not have to be completely straight, but the inlets in a row may e.g. be arranged in a zigzag pattern along a straight imaginary line in order to save space. For the same reason, this is also applicable to a row of sources.

Instead of having several sets of, preferably parallel, rows of collimator passage inlets, each set with different size of generated beam, it would also be conceivable to provide only one set, i.e. only one size of beam, with several rows of collimator passage. This too would enable a change of spatial dose distribution as will be described.

The sources, or at least a subset thereof, may be displaced in a direction substantially perpendicular to and intersecting said rows of collimator passage inlets. If several sets (different beam sizes) of collimator passages are provided, such a displacement would allow a change from one set to another set, thereby changing the beam sizes and thus the spatial dose distribution surrounding the focus. A further feature of such a motion, which may also be useful when only a single set (one beam size) of rows of collimator passages are provided, is when one or more rows of sources are displaced past an end row of collimator passage inlets. This will result in one or more rows of sources being blocked or shut off while the rest of the rows of the sources will be in register with one or more rows of collimator passage inlets. This may be useful if a certain part of the patient is to be protected, for instance the eyes, or for any other reason when the dose gradient is to be changed.

The present invention enables the relative displacement of said subset of sources to be an essentially straight, i.e. linear, motion. It should be clear that a linear or translational displacement of the sources is a completely different approach compared with the traditional prior art devices presenting a rotational motion. Even though a linear displacement has many advantages, the present invention does not exclude, as an alternative a curved or rotational motion, or even a combined linear and rotational motion. When segments are used, as has been described above, they are preferably displaceable along the envelope surface or lateral area of the collimator body, this suitably applying to a linear as well as a curved displacement. In other words the sources are maintained at a substantially constant level relative to the collimator body, i.e. they are not lifted from the collimator body in this context.

A radiation therapy device enabling a linear displacement, i.e. a uniform motion in a straight line, of said subset of sources provides good operational liability. The linear motion allows the provision of reliable and rigid end positions, such as by mechanical means, e.g. comprising a rigid and precise bearing arrangement. Thus, the positioning of the sources in relation to the collimator passage inlets is facilitated. Also, the use of a linear displacement allows for an arbitrary form of the treatment space to be chosen and still have an optimal radiation protection. Furthermore, a linear motion generally requires less energy for acceleration and retardation than a rotational one for a large diameter.

A linear displacement of at least a subset of sources in relation to at least a subset of collimator inlets enables at least one or more, or even all, of said sources to be shut off, i.e. not being in register with the collimator inlets.

It is to be understood that the linear displacement of the sources relatively to the collimator passage inlets may be accomplished by moving the sources while keeping the inlets still, or moving the inlets, i.e. at least a portion of the collimator body, while keeping the sources still, or by simultaneously or consecutively moving both the sources and the inlets. The linear displacement may be implemented by means of various actuator means.

The linear displacement may be performed in various directions. Linear displacement can be defined in the following way. First two coordinate systems, such as Cartesian coordinate systems, are defined, one for each object which is involved in the relative displacement. For instance, a subset of sources may be considered to be arranged in a first coordinate system, and a subset of collimator passage inlets may be considered to be arranged in a second coordinated system. When said objects (e.g. subsets) are displaced relatively to each other, while assuming that the respective coordinate systems follow the movement of the objects, i.e. each object will have an unchanged location and orientation in its own coordinate system, said displacement will be linear if the angle of the first coordinate system to the second coordinate system (or respective coordinate axes thereof) remains unchanged. In other words the coordinate systems can be regarded as performing a relative movement, carrying the objects along, without a change of angle. In contrast to a linear displacement, a rotational displacement would result in a change of angle of the coordinate systems or a change of location or orientation of the objects in the coordinate system.

According to at least one embodiment of the invention the source carrier arrangement, and the collimator body has a cross-section of at least an arc of a circle, preferably an entire circle, the sources and the collimator body inlets being distributed circumferentially along the circle or the arc of a circle. The linear displacement may in such a case be performed in a direction substantially perpendicular to said cross-section, i.e. substantially parallel with the center axis of the circle or arc of the circle. The center axis may also be described as the z-axis in a cylindrical r-, φ-, z-coordinate system. The sources and the collimator passage inlets are in such a coordinate system distributed at least in the φ-direction (angular direction). The collimator passage inlets and sources are linearly displaceable relatively to each other in parallel to the z-axis (center axis). There may, however, be an inclination of the direction of displacement. relatively to the center axis, as will be described later on.

The center axis may coincide with the z-axis in the Leksell x-, y-, z-coordinate system, which is a Cartesian coordinate system and in which the x-axis extends in parallel to a line drawn from one ear to the other ear of the patient, the y-axis extends in parallel to a line drawn from the neck to the nose of the patient, and the z-axis extends in parallel to the longitudinal direction of the patient's body. However, the patient may be tilted relatively to the center axis, wherein the linear displacement in the above described case may be defined in relation to said Leksell z-axis rather than the center axis. Thus, the linear displacement may be parallel with said Leksell z-axis, or somewhat inclined relatively to said Leksell z-axis. In case of an inclined linear direction, that direction would preferably intersect the center axis or the Leksell z-axis, which may be the case when a somewhat conical source carrier arrangement is used, as will be described later on.

The cross-sections of the collimator body and the source carrier arrangement do not have to be circular, they could define a polygon, such as a rectangle, a pentagon, a hexagon, a heptagon, an octagon, etc. The sources could be displaceable, like in the examples above, essentially perpendicularly to said cross-section, or they could be displaced tangentially, i.e. along a side of the polygon. It is to be understood that the collimator body and the source carrying arrangement may describe a part of a polygon, i.e. an open cross-section, such as a hexagon cut in half.

As has been previously mentioned the source carrier arrangement may have a somewhat conical shape. Thus, according to at least one embodiment of the present invention at least a portion of the source carrier arrangement has an envelope surface or lateral area shaped substantially like a frustum of a cone. The patient's head or body may be introduced into the treatment space through the base of said cone. Source carrier arrangement segments may be placed in a ring circumferentially along the envelope surface. The segments may be displaceable e.g. on a sliding surface. Since the envelope surface is shaped like a frustum of a cone, the direction of motion of the segments is somewhat inclined relatively to the center axis of the source carrier arrangement, the motion follows the slant of the cone. A typical angle may be in the range of 0–45°, such as 5–25°, preferably 10–15°. The linear direction of motion being such that the segments, when moved away from the patient side, move closer towards the center axis. Even though it may be preferred to have a ring of segments that is only one segment wide, it would be conceivable to have more segments or rings of segments around the envelope surface. For instance, if a segment can be split into two segment parts, one part could be moved towards the base of the cone, while the other could be moved away from the base of the cone. Such a split into segment parts would be conceivable for other shapes of collimator bodies and source carrier arrangements.

Suitably, each segment comprises or is connected to a respective actuator. Such an actuator may comprise an arm, shaft or an axle, including a driving means, such as mechanical, electrical, pneumatic, hydraulic, etc. The linear displacement of the segment is controlled by means of the actuator. The actuator itself could be designed to move in different ways. However, it may be practical to take advantage of a linear movement of an actuator arm, in case of which the direction of motion of the actuator arm would suitably be transmitted to the segment following in the same direction. For a source carrier arrangement having an envelope surface resembling to a cone or frustum of a cone the elongation of each actuator arm would form an angle and intersect with the center axis. In case of a straight cylinder being the form of the source carrier arrangement the elongation of each actuator arm would run in parallel to the center axis.

As has been mentioned previously an alternative to a linear displacement of the radiation sources is a curved or rotational displacement. In such case, suitably, each segment is displaceable along a curvature such as along an arc of a circle.

For instance, according to at least one embodiment of the invention, when the collimator body is of substantially hemispherical shape with an open annular base through which the patient's body or preferably at least the head may be introduced, each segment may be displaceable in a rotary motion in relation to an axis extending along the diameter of the annular base. As a segment is displaced its distance to the crest of the hemisphere will be changed during the motion. Generally, this means that the sources may be rotated around the x-axis in the Leksell x-, y-, z-coordinate system as they follow the surface of the hemisphere.

As an alternative, in case of a hemispherical collimator body being used, the axis of rotation may instead be essentially perpendicular to the above mentioned axis. More specifically, the axis of rotation may extend from the center of the annular base to the crest of the hemisphere. Generally, this means that the sources are rotated around the z-axis in the Leksell x-, y-, z-coordinate system. As a segment is displaced its distance to the crest of the hemisphere will remain essentially constant during the motion.

It is to be understood that other inclinations of the axis of rotation may be arranged, including something between the two above mentioned axes. It should also be understood that the term substantially hemispherical comprise also somewhat smaller part of a sphere, and also a somewhat larger part of a sphere.

A hemisphere has a cross-section of a circle if said section is parallel to the base plane of the hemisphere, or an arc of a circle if said section is perpendicular to the base plane of the hemisphere. Such cross-sections are also obtainable for a cylindrically curved shape. Therefore, according to at least a further embodiment of the invention, the collimator body has a cross-section of at least en arc of a circle, preferably an entire circle. The sources and the collimator passage inlets are distributed along said arc of a circle, wherein each segment is displaceable along said arc of a circle or circumference of the circle.

The rotational or curved displacement of the segment may be actuated by various actuating means, such as for instance by means of motor driven crankshafts brought into rotation.

From the description above it should be clear that the present invention provides different alternatives for the design of a radiation therapy device. However, they all have in common the inventive concept of enabling a selection of radioactive sources to be displaced during operation of the device, while the other radioactive sources are kept in position. Such a displacement may be performed for a source carrier arrangement in the form of an advantageous linear motion or as alternatively in the form of a curved motion. The source carrier arrangement suitably comprises several segments which may be partly connected to each other or completely separated from each other. Some embodiments will be further discussed in the following description of the drawings.

DETAILED DESCRIPTION OF THE DRAWINGS

Figure 1:
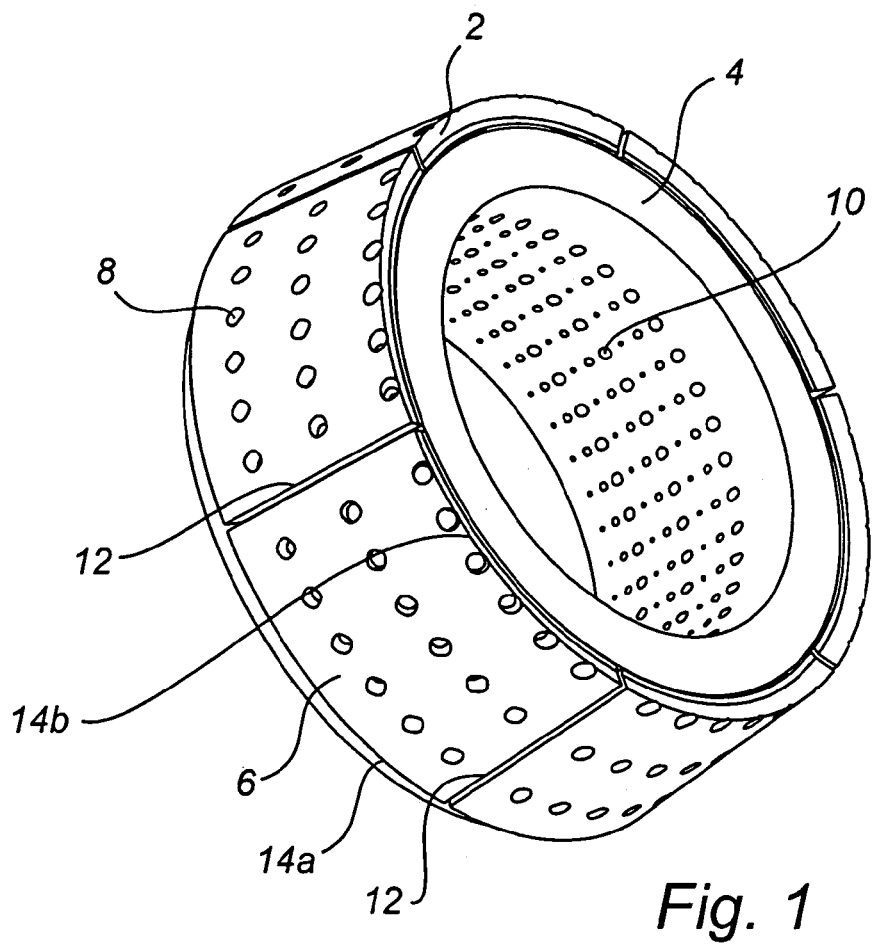
FIG. 1 is a perspective view of an assembly comprising a source carrier arrangement surrounding a collimator body, in accordance with an embodiment of the invention.

FIG. 1 is a perspective view of an assembly comprising a source carrier arrangement 2 surrounding a collimator body 4, in accordance with an embodiment of the invention. The source carrier arrangement 2 and the collimator body 4 both have the shape of a frustum of a cone. The source carrier arrangement 2 comprises six segments 6 distributed along the annular circumference of the collimator body 4. Each segment 6 has a plurality of apertures 8 into which containers containing radioactive sources, such as cobalt, are placed. The collimator body 4 is provided with collimator passages or channels, internal mouths 10 of said channels are shown in the figure.

Each segment 6 has two straight sides 12 and two curved sides 14a, 14b. One of the curved sides 14a forms a longer arc of a circle, and is located near the base of the cone, while the other curved side 14b forms a shorter arc of a circle. The segments 6 are linearly displaceable, that is they are not rotated around the collimator body 4, but are instead movable back and forth along an imaginary line drawn from the center of the shorter curved side 14b to the center of the longer curved side 14a. Such a translation displacement has the effect of a transformation of coordinates in which the new axes are parallel to the old ones.

Due to the conical shape of the assembly, neighbouring segments are spaced apart by a gap, at least when being placed closest to the longer curved side 14a, so as to enable the linear displacement. The possible distance of motion for a segment is suitably set by two stop members (not shown), one at each curved side. In an end position, i.e. when the segment 6 is in contact with one of said stop members, the sources of said segment will be in a shut off state, which means that the sources are not in register with any collimator passage inlets.

A spring means (not shown) may be provided for each segment 6, said spring means striving to push the segment 6 toward one of the stop members. This is advantageous in case of a power failure, i.e. absence of current, in which case the spring means will push the segment 6 toward the stop member, thereby ensuring that the sources are not in register with any collimator passage inlet and the risk of radioactive leakage is minimized.

Furthermore one of the stop members may be used as a reference point or point of zero, from which the segment 6 is displaceable.

As can be seen from FIG. 1 there is a larger number of internal mouths 10 or holes of the collimator passages than the number of apertures 8 for receiving radioactive sources. In this particular case there are three times as many collimator passages as there are apertures for receiving radioactive sources, such as e.g. 180 apertures and 540 collimate or passages. The reason for this is that there are three different sizes of collimator passages in the collimator body 4, or rather passages which direct radiation beams with three different diameters, toward the focus. Said diameters may e.g. be 4, 8 and 14 mm. The three different types of collimator passages are each arranged in a pattern which corresponds to the pattern of the apertures in the source carrier arrangement. The desired size or type of collimator passage is selected by displacing the segments 6 of the source carrier arrangement linearly along the collimator body so as to be in register with the desired collimator passages.

Figure 2:
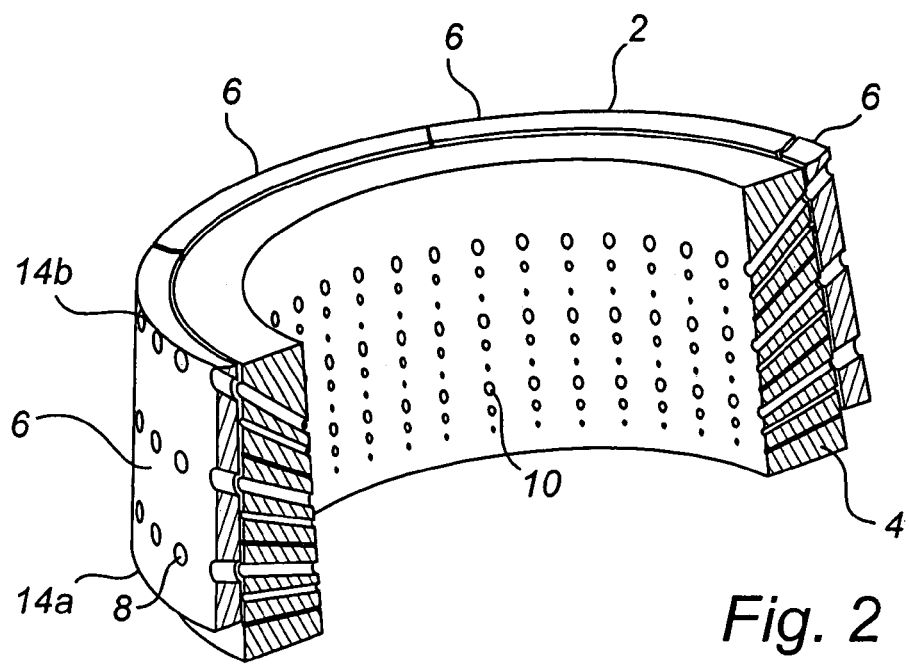
FIG. 2 is sectional view in perspective of the assembly shown in FIG. 1.

FIG. 2 is sectional view in perspective of the assembly shown in FIG. 1. The same reference numerals are used for details which are the same as in FIG. 1. This also applies to the following FIGS. 3 and 4.

Figure 3:
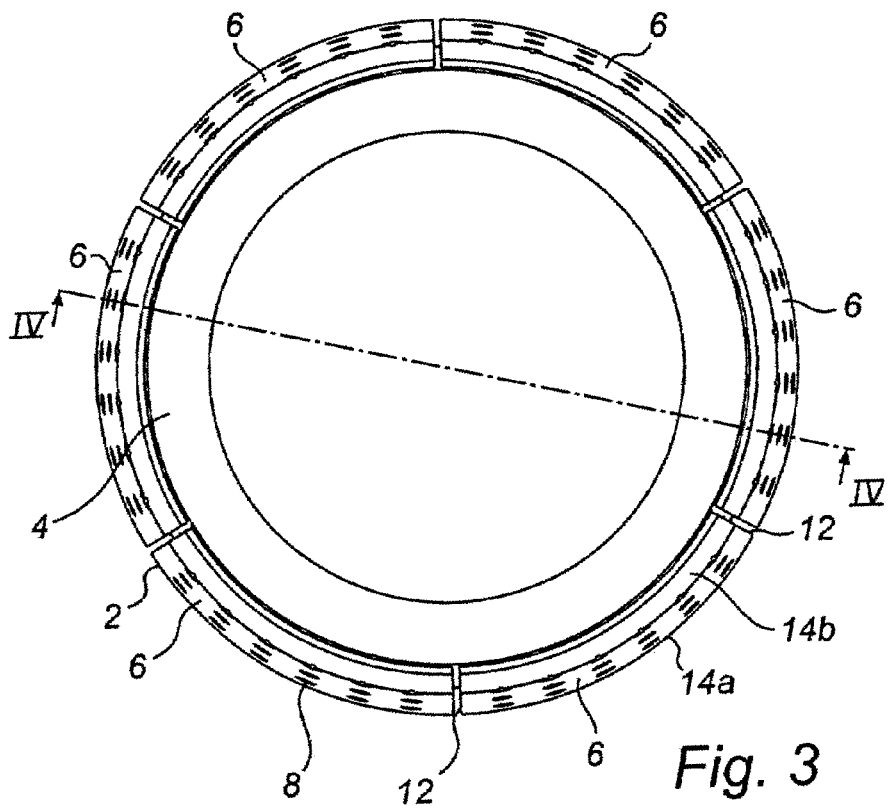
FIG. 3 is a view from the backside of the assembly shown in FIG. 1.

FIG. 3 is a view from the backside of the assembly shown in FIG. 1. This is the side with smaller diameter, while the other side, having a larger diameter, is the front or patient side, i.e. where the patient's body is introduced.

Figure 4:
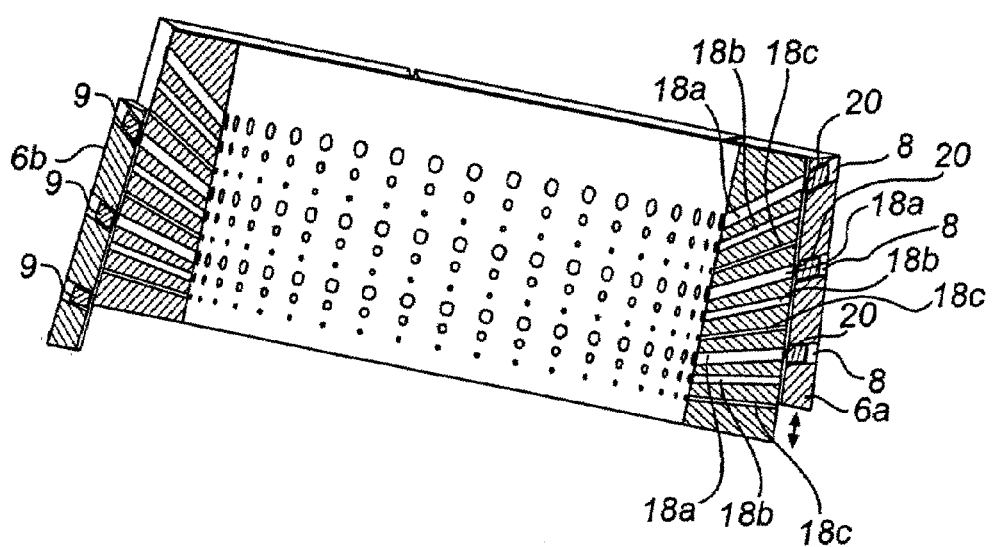
FIG. 4 is a view in cross-section along line IV—IV in FIG. 3.

FIG. 4 is a view in cross-section along line IV—IV in FIG. 3. Thus, in FIG. 4 two segments 6a and 6b are shown. Starting with one of the segments 6a, in this view it can be seen that there are nine collimator passages 18a–18c available for three radioactive sources 9 contained in a respective aperture 8 in the source carrier arrangement. The sizes of the collimators 18a–18c are arranged in an alternating sequence, such as for instance, the first collimator passage 18a providing a beam of 14 mm in diameter, the second collimator passage 18b providing a beam of 8 mm in diameter, the third collimator passage 18c providing a beam of 4 mm in diameter, the fourth collimator passage 18a starting the sequence all over by providing a beam of 14 mm in diameter, etc. However, the collimator passages 18a–18c could, alternatively, be arranged in another order, e.g. to provide the sequence 14 mm, 4 mm, 8 mm. In the figure the apertures 8 of the source carrier arrangement are arranged in register with the first, fourth and seventh collimator passages 18a, or rather their respective inlets, said collimator passages all providing a beam of 14 mm in diameter at the focus. Each segment may be individually displaced in a straight direction as is illustrated with the double-headed arrow in order to select another group of collimator passages, i.e. another beam diameter size for any segment. If the segment is displaced so that the radioactive sources 9 face a surface in between the collimator passages, those radioactive sources will be shut off, i.e. essentially no or only a minimum radiation from those sources will reach the focus. A segment may also like the segment 6b in FIG. 4 be displaced to such an extent that one of the three shown apertures will be located beside and outside of the first or ninth collimator passage. This allows of the possibility to arrange only two of the three radiation sources 9 in register with two collimator passages. Thus, this and other embodiments do not only enable that differently sized beams are simultaneously directed from different directions toward a common focus, but also that different numbers of beams may simultaneously be directed from different directions.

As can be seen in FIG. 4 the nine collimator passages 18a–18c are arranged at somewhat different angles in order for the beams to be directed to the common focus, regardless of which collimator passage or passages that are used at the moment. The angle of extension direction of the first to the last collimator passage having the same cross-section is, in this case, at least 30°.

An advantage of the conicity of embodiments such as the one illustrated in FIGS. 1–4 is that the solid angle of the sources is spread out. The beams passing through the patient's tissue on their way towards focus will be evenly distributed. Furthermore, each source will have substantially the same distance to the focus, which is advantageous since the intensity of the source is reversibly proportional to the square of the distance between the radioactive source and the focus.

Another advantage of this and other embodiments of the invention is that the fixed collimator body 4, even though having a multiplicity of fixed collimator passages, still enables a complete or merely a partial shut off of the radioactive sources.

Figure 5:
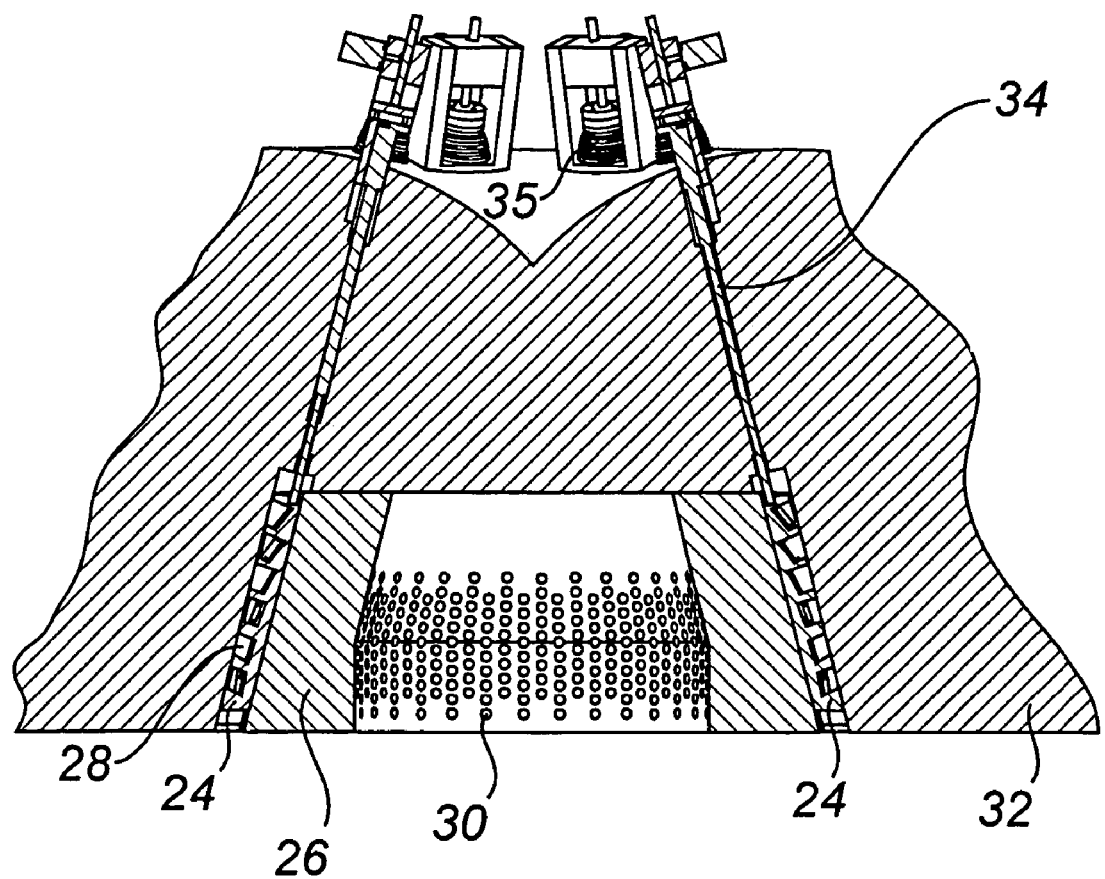
FIG. 5 is a sectional view of an assembly of the type shown in FIGS. 1–4, said assembly being illustrated with an actuating mechanism and a rear radiation protection structure.
Figure 6:
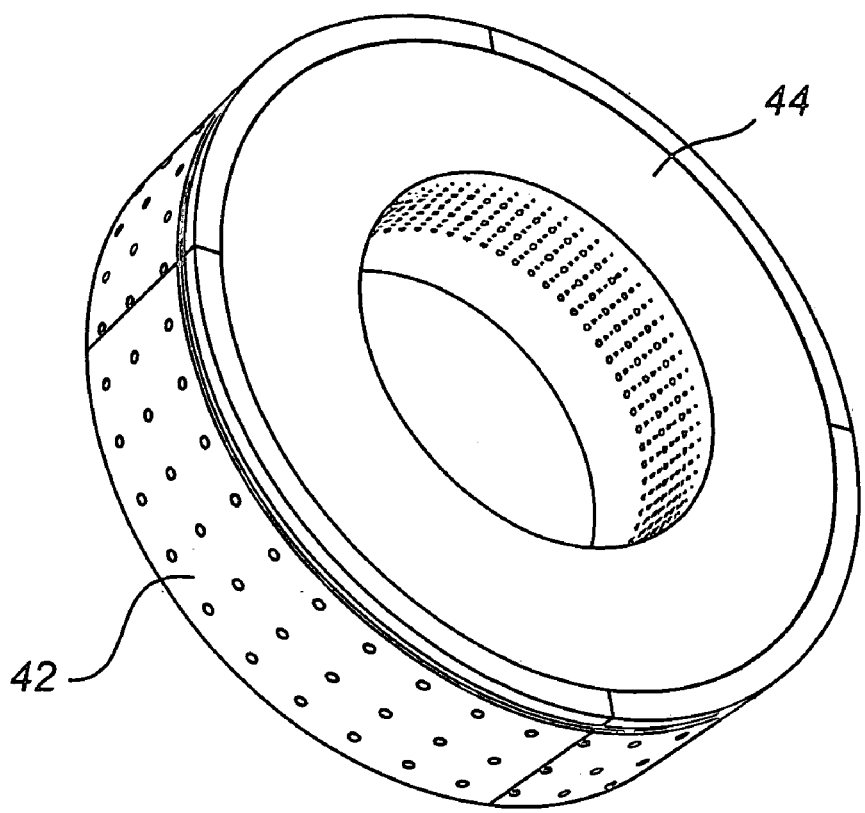
FIG. 6 is a perspective view of an assembly comprising a source carrier arrangement surrounding a collimator body, in accordance with a second embodiment of the invention.

FIG. 5 is a sectional view of an assembly of the type shown in FIGS. 1–4, said assembly being illustrated with an actuating mechanism and a rear radiation protection structure. Accordingly, a source carrier arrangement having a plurality of segments 24 is provided. Each segment 24 has a number of apertures 28 in which sources are inserted. The segments 24 are arranged around a collimator body 26 having collimator passages (not shown) with mouths 30 directing radiation beams towards a focus.

The segments are surrounded by a rear radiation protection structure 32, so as to minimize or eliminate leakage of radiation to the nursing personnel. The rear protection structure 32 is dimensioned and made of a suitable material, such as casting material, accordingly. A front radiation protection structure (not shown) is suitably also provided, preferably of smaller dimension so as to facilitate access to the treatment space, but with a high density material, such as lead, tungsten or depleted uranium.

An actuating mechanism is provided for displacing the segments in a linear direction of motion. The maximum displacement distance for a segment may e.g. be 60 mm, however larger or smaller distances are also conceivable. The actuating mechanism comprises a number of supporting rods or arms 34, each arm being connected to a respective segment 24. The arms 34 extend through a respective bore in the rear radiation protection structure 32 and are movable along their direction of elongation. The arm and the bore are designed so as to form a labyrinth passage having different portions of overlapping diameters, thereby minimizing or eliminating the escape of hazardous radiation through the bore. Each arm is individually controlled by means of a respective rotational electrical motor. The electrical motor has a high resolution with a positioning encoder and a ball roller screw enabling a precise linear positioning of the arm 34 and the segment 24. A spring means 35 is arranged to affect the arms and ensure that they displace the segments so that the radioactive sources will be in a complete shut-off position in case of power failure. The arms 34 may be disconnected from the segments 24, when the segments are to be provided with new radioactive sources. In such case the loading is suitably done through channels (not shown) provided in one area of in the rear radiation protection structure 32. The loading procedure may be performed in a conventional manner as in the prior art, e.g. a procedure corresponding to the one used in connection with Leksell Gamma Knife®. However, alternative procedures are also conceivable.

Figure 7:
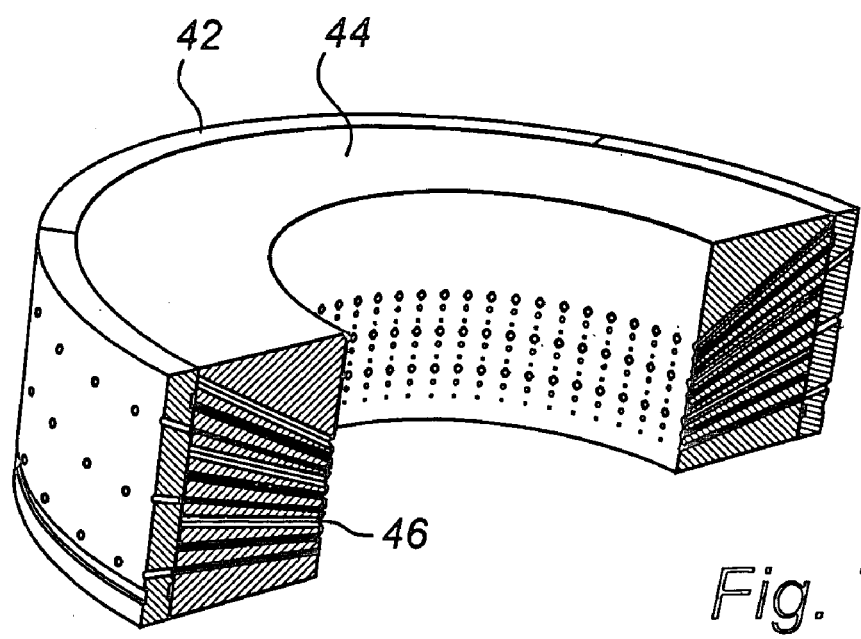
FIG. 7 is a sectional view in perspective of the assembly shown in FIG. 6.
Figure 8:
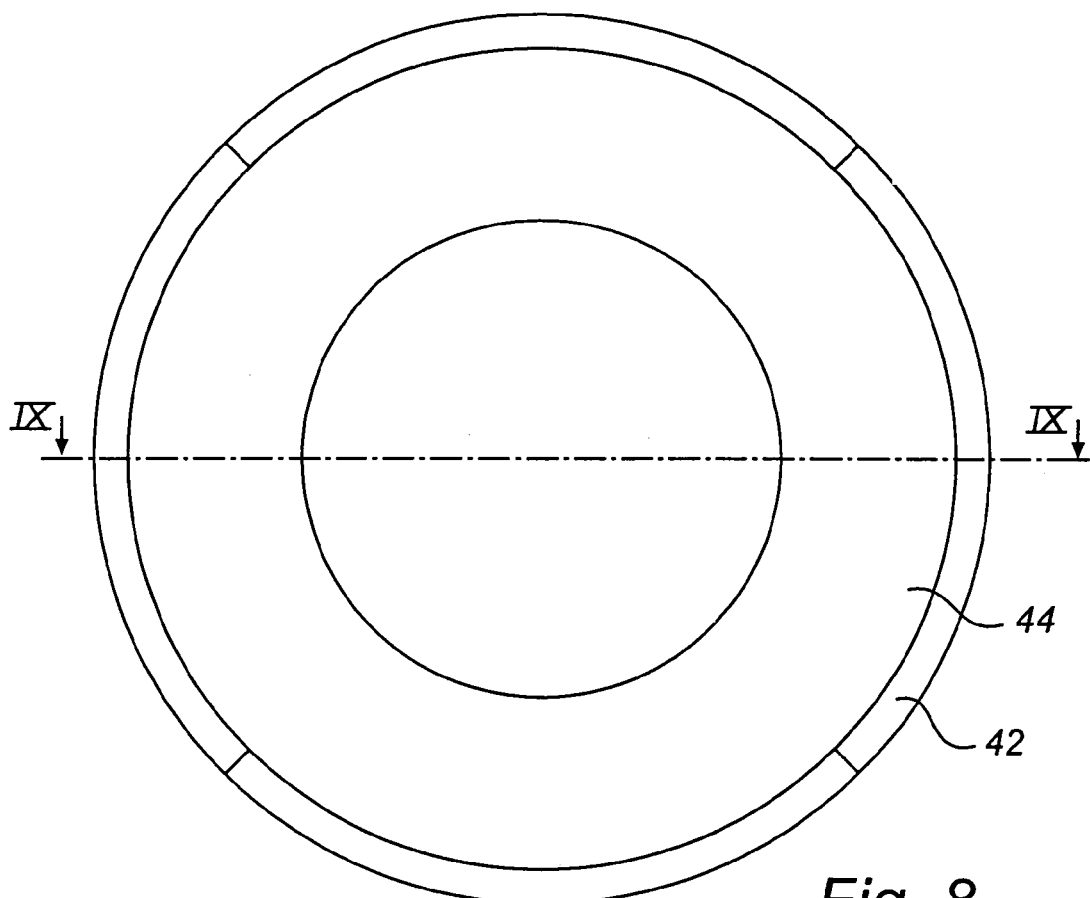
FIG. 8 is a view from the backside of the assembly shown in FIG. 6.
Figure 9:
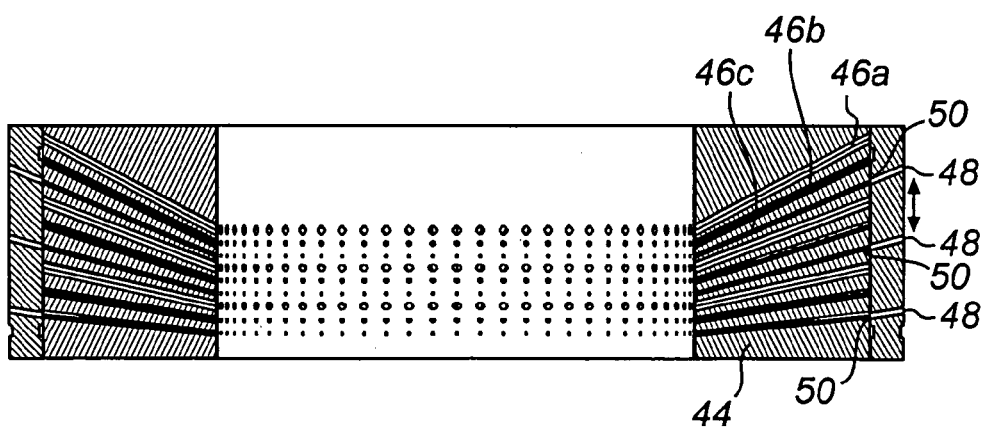
FIG. 9 is a view in cross-section along line IX—IX in FIG. 8.
Figure 10:
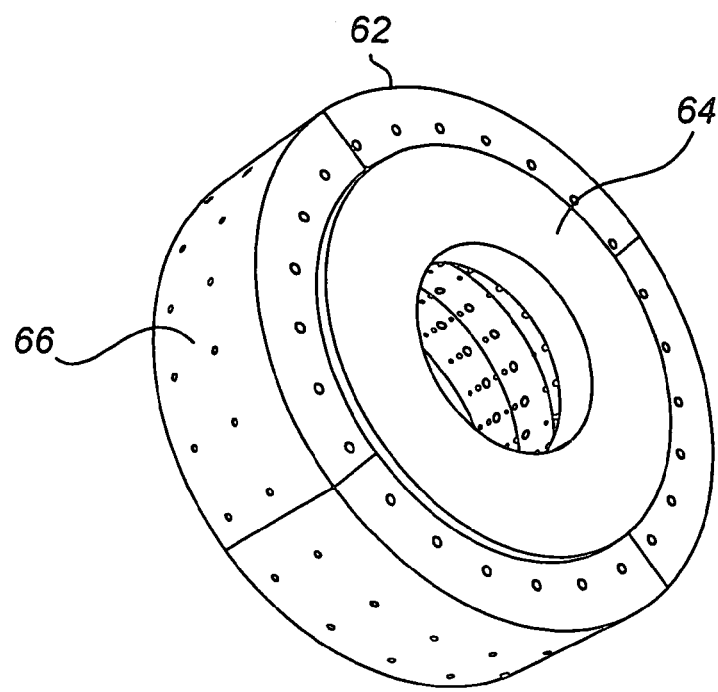
FIG. 10 is a perspective view of an assembly comprising a source carrier arrangement surrounding a collimator body, in accordance with a third embodiment of the invention.
Figure 11:
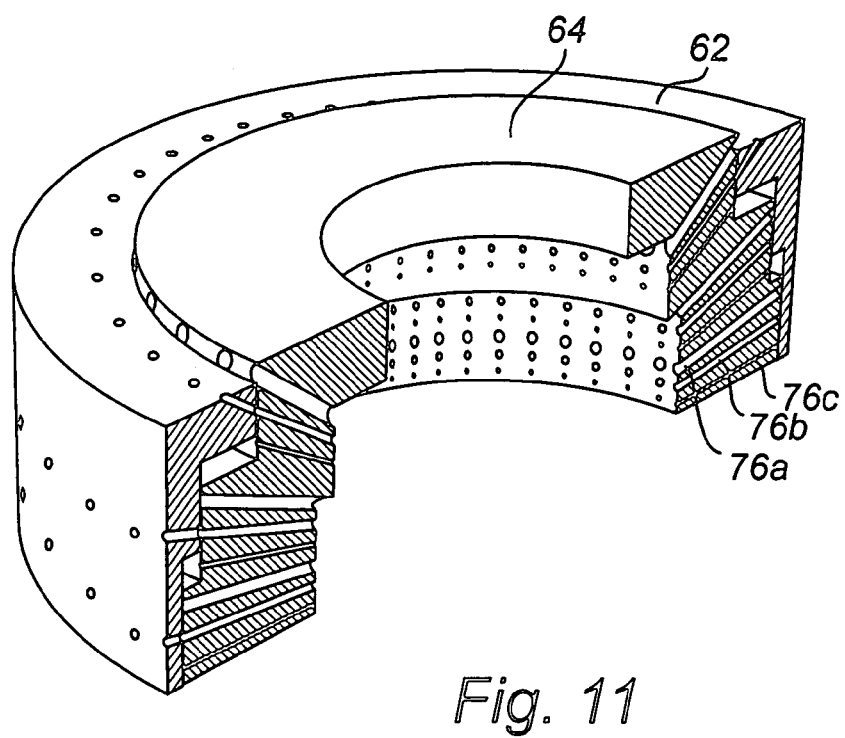
FIG. 11 is sectional view in perspective of the assembly shown in FIG. 10.
Figure 12:
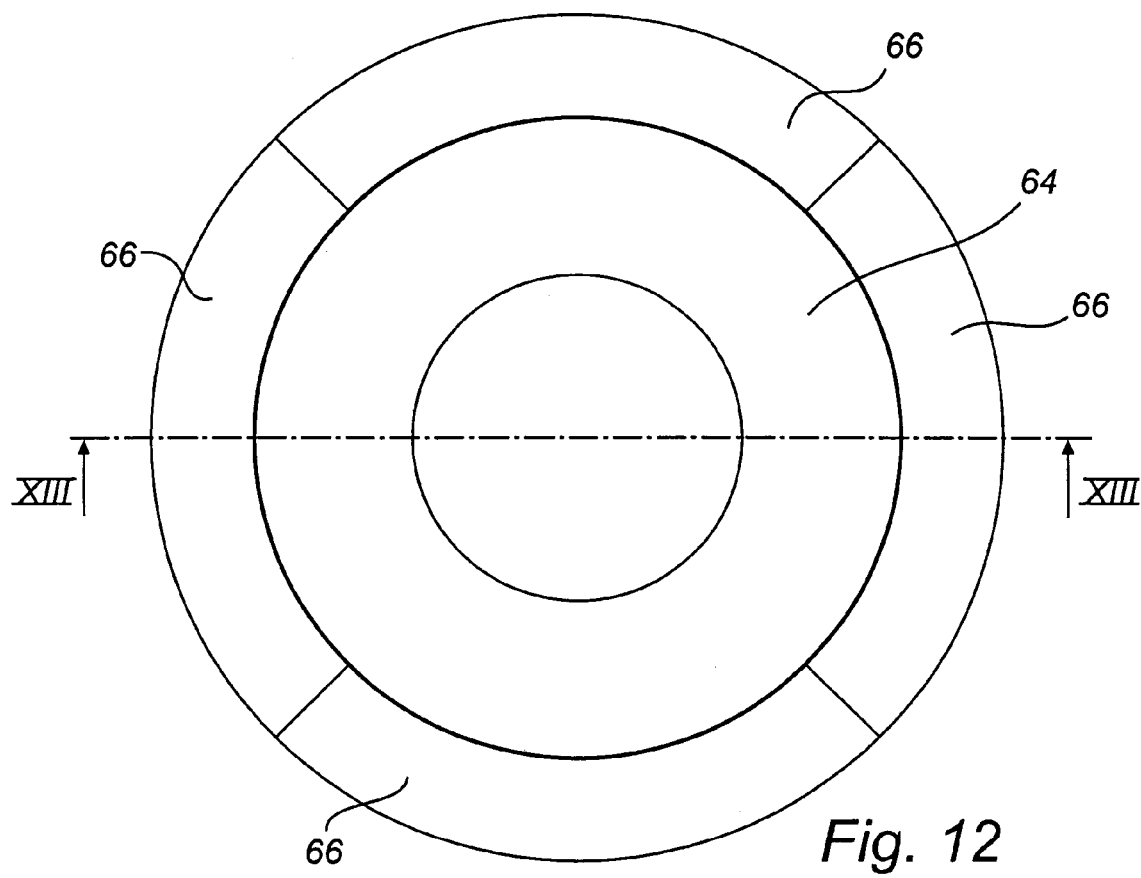
FIG. 12 is a view from the backside of the assembly shown in FIG. 10.
Figure 13:
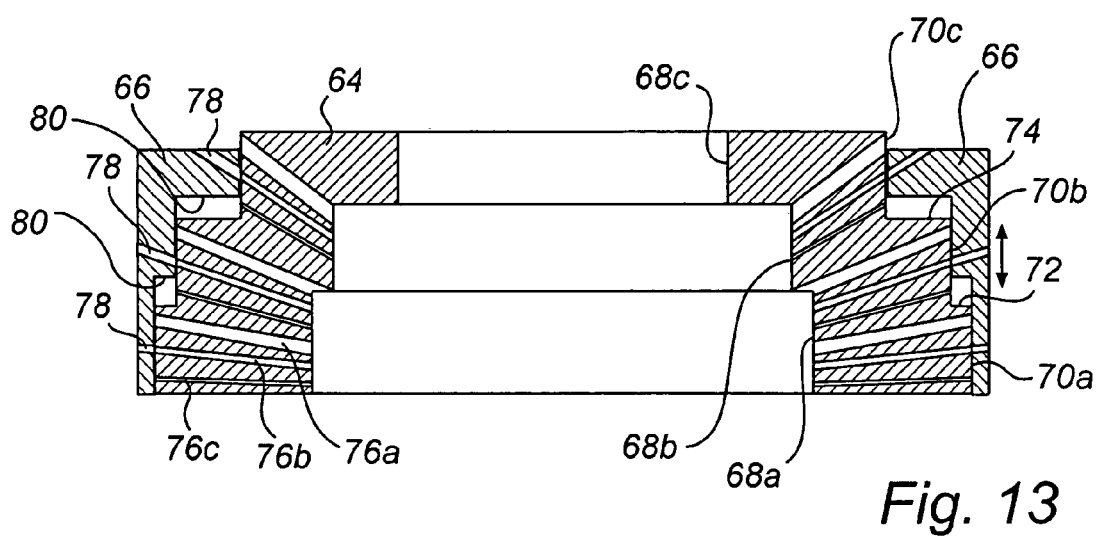
FIG. 13 is a view in cross-section along line XIII—XIII in FIG. 12.

FIGS. 6–9 illustrate, in views corresponding to FIGS. 1–4, respectively, an assembly comprising a source carrier arrangement 42 surrounding a collimator body 44, in accordance with a second embodiment of the invention. As can be seen in FIGS. 6–9, the collimator body 44 has the shape of a straight circular cylinder. The surrounding source carrier arrangement 42 comprises four segments with radioactive sources and has similarly the shape of a straight circular cylinder. It can be noted that the section in FIG. 7 is taken through a portion of the collimator body comprising collimator passages 46. These collimator passages are also shown in FIG. 9 which is a sectional view along line IX—IX in FIG. 8. Due to the three different sizes of collimator passages they are denoted 46a, 46b, 46c and are arranged in alternating series like the collimator passages previously shown in FIG. 4. Also the source carrier arrangement, which is movable as indicated by the double arrow, has in the shown section three apertures 48 for radioactive sources. The source carrier arrangement is positioned so that the apertures 48 are in register with inlets 50 to the smallest diameter collimator passages 46c.

FIGS. 10–13 illustrate, in views corresponding to FIGS. 1–4, respectively, an assembly comprising a source carrier arrangement 62 surrounding a collimator body 64, in accordance with a third embodiment of the invention. As can be seen from FIGS. 10–13 the source carrier arrangement 62 comprises four segments 66. The collimator body 64 has the form of a stepped cylinder, i.e. it comprises concentric portions of different diameters, the largest diameter being at the patient or front side and the smallest diameter being on the backside. In the particular embodiment shown in FIGS. 10–13 the collimator body has three step portions 68a–68c. The first step portion 68a is nearest the patient side and has the largest outer diameter, said outer diameter being defined by a first sliding surface 70a. The second step portion 68b is located adjacent to the first step portion 68a and has a somewhat smaller outer diameter. Due to the difference in outer diameter a circular first shoulder 72 is defined on the first step portion 68a, said first shoulder 72 being in one piece with a thereto perpendicular second sliding surface 70b of the second step portion 68b. Similarly, a third step portion 68c is located adjacent to the second step portion 68b with an even smaller outer diameter defined by a third sliding surface 70c which is perpendicular to a second shoulder 74 defined on the second step portion 68b.

In a cross section (se e.g. FIG. 13) the first, second and third step portion each have three collimator passages inlets leading to collimator passages 76a–76c which direct radiation beams toward a substantially common focus. Furthermore, in each step portion 68a–c the three collimator passages 76a–76c are of different diameters.

The source carrier arrangement 62 comprises four segments 66, each segment 66 carrying a number of sources. As can be seen from e.g. FIG. 13 in a cross section a segment 66 of the source carrier arrangement has three sliding surfaces which mate the sliding surfaces 70a–70c of the collimator body. Each sliding surface of a segment 66 comprises in the shown cross-section a radioactive source aperture 78 which is placeable in register with one of the collimator passage inlets on the corresponding sliding surface of a collimator step portion 68a–68c. The first and second shoulder 72, 74 on the first and second step portion 68a, 68b, respectively, of the collimator body 64 function as stop faces against corresponding areas 80 of the segments 66 of the source carrier arrangement, and thereby defining an end position to which it is possible to displace the segments. A double arrow indicates the direction of displacement.

It is to be noted that this, as well as any other embodiment, may suitably be provided with slide bearings in order to facilitate the displacement of the source carrier arrangement by sliding on the collimator body. In this connection should also be noted that the present invention allows the radioactive sources to be placed close to and almost in contact with the inlets of the collimator passages.

Figure 14:
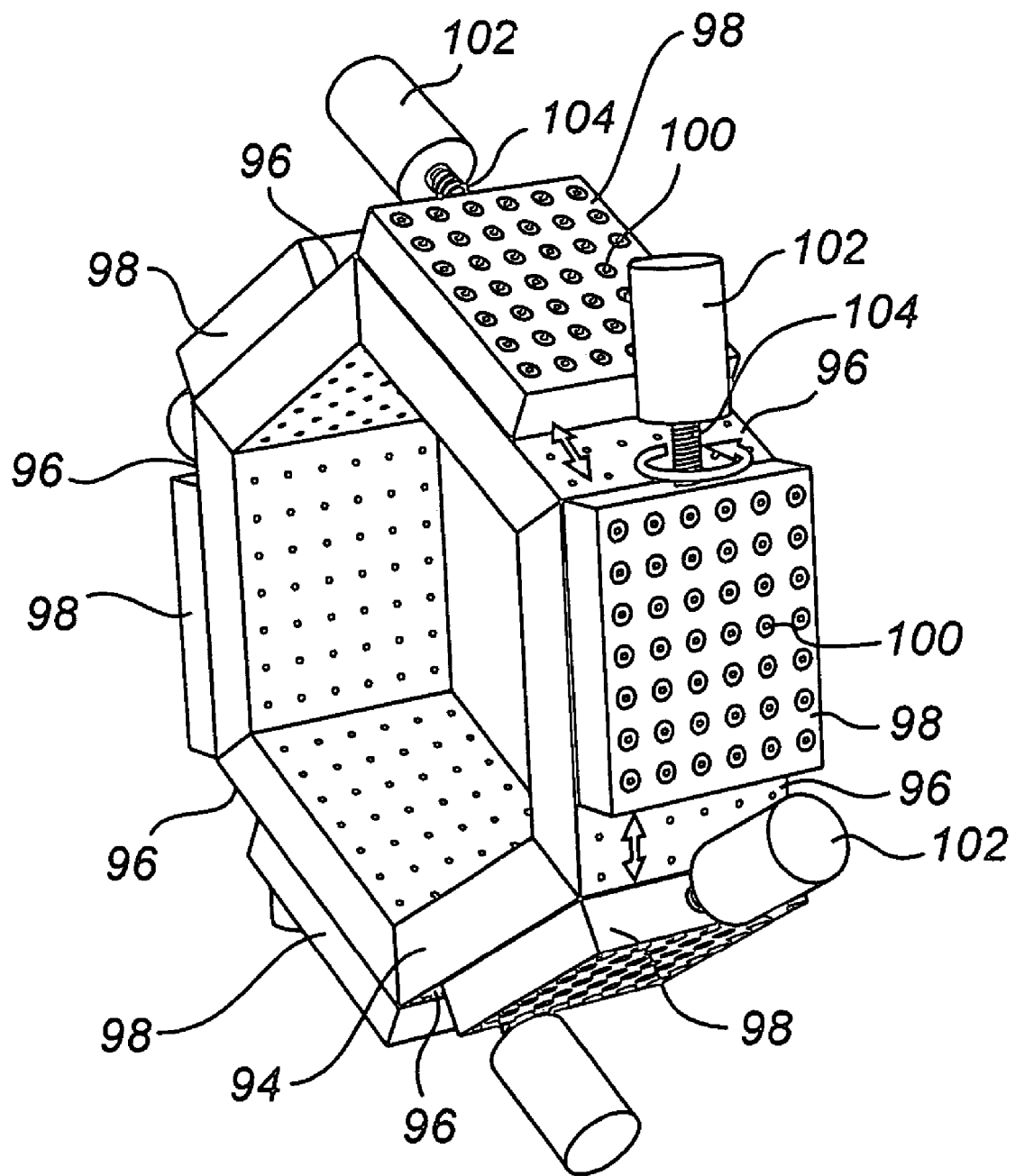
FIG. 14 is a perspective view, partly in cross-section, of an assembly comprising a source carrier arrangement surrounding a collimator body, in accordance with a fourth embodiment of the invention.

FIG. 14 is a perspective view, partly in cross-section, of an assembly comprising a source carrier arrangement surrounding a collimator body 94, in accordance with a fourth embodiment of the invention. The collimator body 94 has the shape of a hexagonal cylinder. Thus, the envelope surface of the collimator body 94 has six faces 96.

This embodiment has two clear differences compared to the previously shown embodiments. One difference is that the source carrier arrangement surrounding the collimator body comprises six clearly separate segments 98. The previous embodiments were also illustrated with individual segments, however they still appeared to form a rather united geometrical figure, while in this embodiment there is less unity and it is the imaginary extensions of the segments 98 that form a geometric figure, i.e. a hexagon.

A second difference of the embodiment shown in FIG. 14 compared with the previously shown figures is that the segments 98 are linearly displaceable in a tangential direction, i.e. perpendicularly to the central axis of the hexagonal assembly. A respective segment 98 which carries sources 100 is displaceably provided on each one of the six faces 96 of the collimator body 94. Thus, each segment 98 may be moved on the corresponding specific face 96 of the collimator body 94 in a direction from one neighbouring face to the other neighbouring face of said specific face. As is illustrated in this figure, the movement of a segment may be affected by means of an actuator 102 comprising a threaded arm 104 which extends into a correspondingly threaded bore (not shown) in the segment 98. By rotating the arm 104 clockwise the segment 98 will be displaced in one direction, and by rotating the arm 104 anticlockwise the segment 98 will be displaced in the opposite direction.

Figure 15:
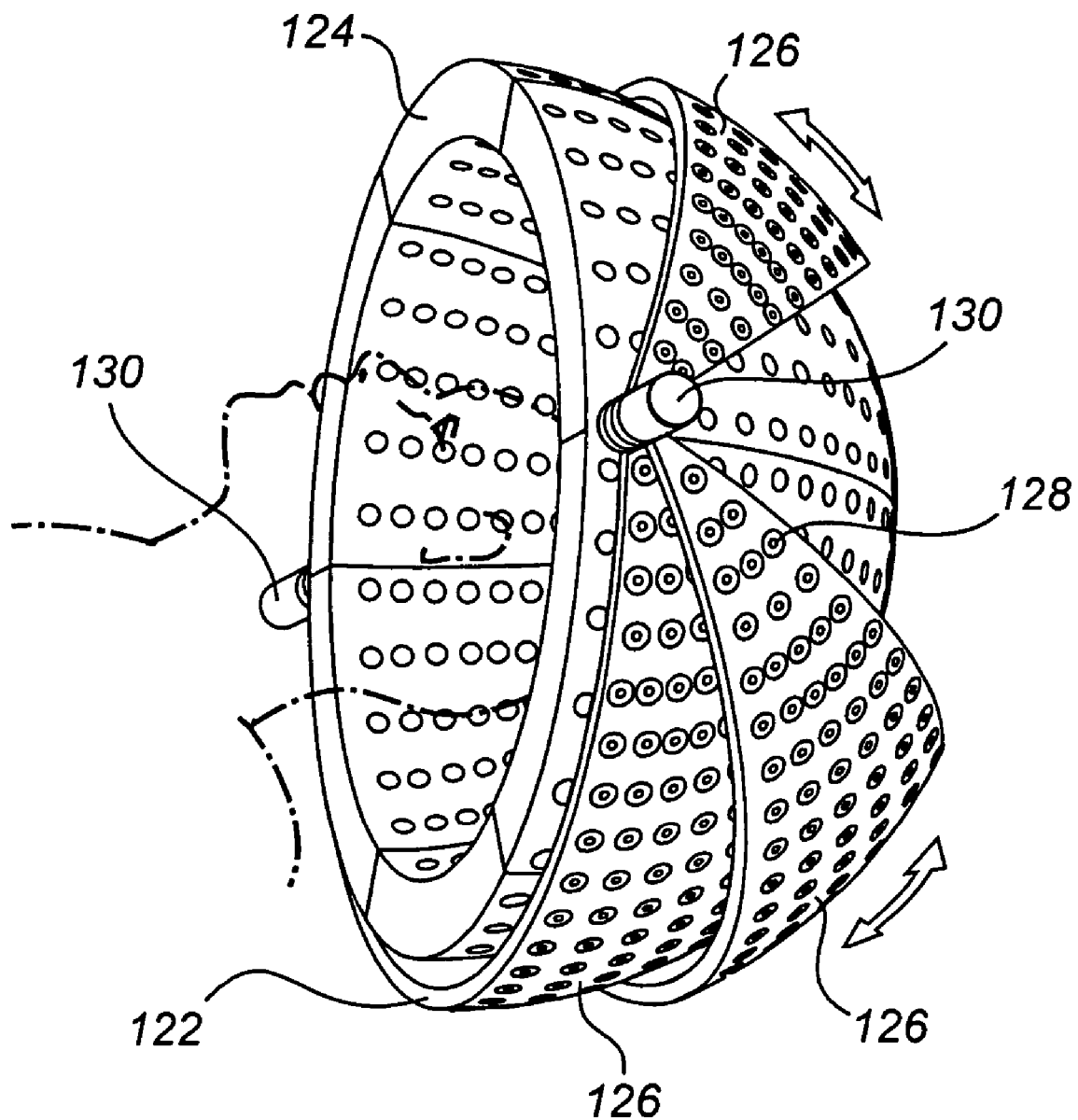
FIG. 15 is a perspective view of an assembly comprising a source carrier arrangement surrounding a collimator body, in accordance with a fifth embodiment of the invention.

FIG. 15 is a perspective view of an assembly comprising a source carrier arrangement 122 surrounding a collimator body 124, in accordance with a fifth embodiment of the invention. The collimator body 124 has the shape of a hemisphere. A patient's head may be introduced, for the purpose of radiation therapy, through the open circular base of the hemisphere. The source carrier arrangement 122 comprises three segments 126 or wings, each being arranged to carry radioactive cobalt sources 128 and each having a bent shape that conforms with the roundness of the collimator body 124. Two shaft units 130 are attached to the collimator body 124, one unit on each side of the patient and essentially in parallel with the Leksell x-axis. Each shaft unit 130 comprises three shafts, namely an inner shaft, a hollow intermediate shaft which surrounds the inner shaft, and a hollow outer shaft which surrounds the intermediate shaft. Each elongate and curved segment 126 has its end portions connected to the shaft units. A first segment is connected to the inner shafts, a second segment is connected to the intermediate shafts, and a third segment is connected to the outer shaft. Thus, a specific segment is individually controllable and displaceable by rotating the respective pair of shafts to which it is connected. Suitably, each pair of shafts is rotated by means of a motor, and may be implemented as a pair of crankshafts.

As can be seen from FIG. 15 the shaft units 130 provide the axis of rotation of the segments 126. Thus, the segments may be rotated along a path extending from one side of the base of the hemisphere over the crest and down to the other side of the base. The three segments 126 are attached at different levels to the shaft units 130, thereby allowing the segments to be positioned over one another if a certain dose distribution is desired. This overlap of segments may be used for shutting off some of the sources. A shut off may also be accomplished without said overlap by rotating a segment to a position where its sources are not in register with collimator passage inlets.

Figure 16:
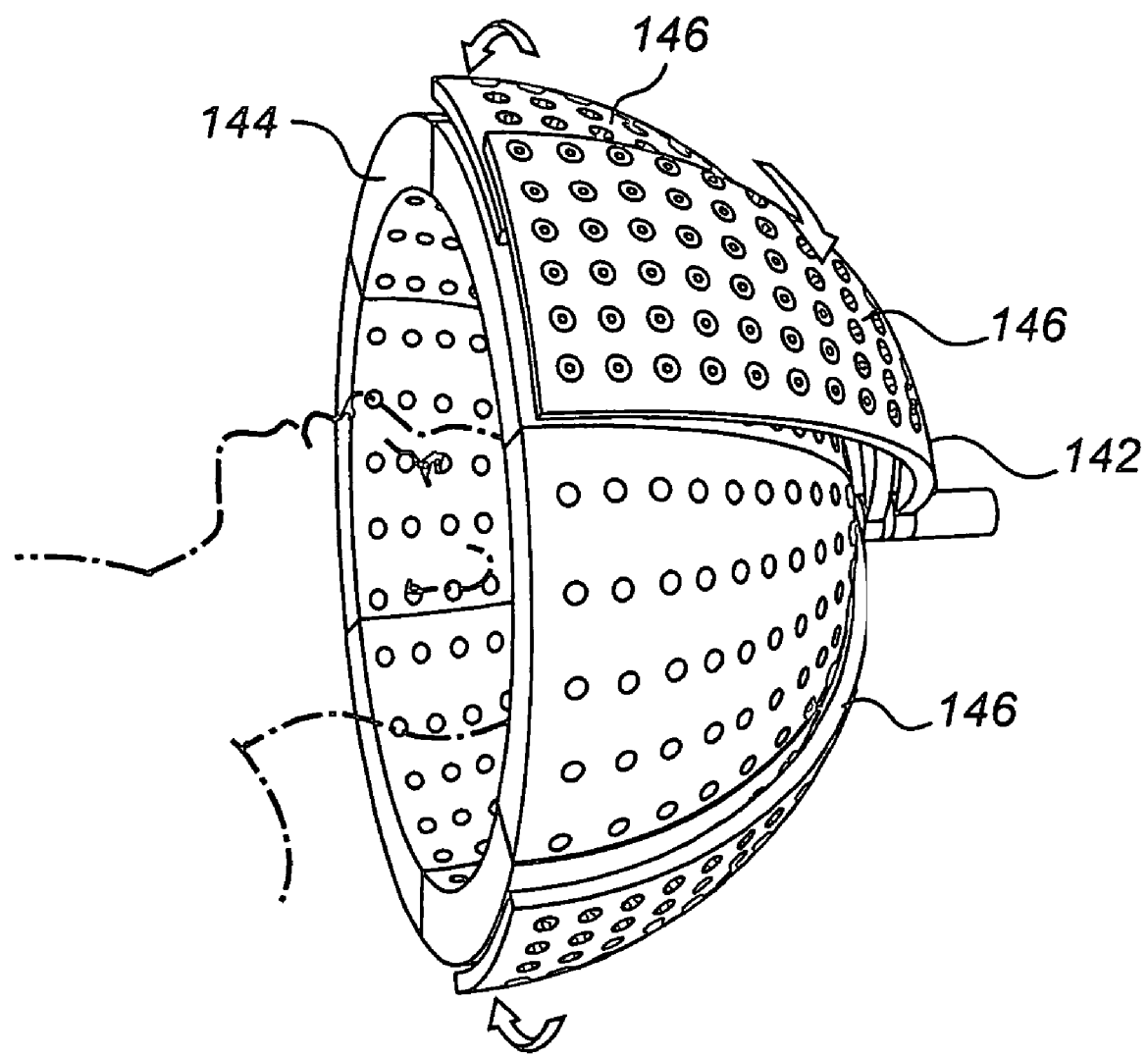
FIG. 16 is a perspective view of an assembly comprising a source carrier arrangement surrounding a collimator body, in accordance with a sixth embodiment of the invention.

FIG. 16 is a perspective view of an assembly comprising a source carrier arrangement 142 surrounding a collimator body 144, in accordance with a sixth embodiment of the invention, which is similar to the embodiment shown in FIG. 15. However, in FIG. 16 the source carrier arrangement 142 comprises three segments 146 which are rotated around another axis, namely the Leksell z-axis.

Figure 17:
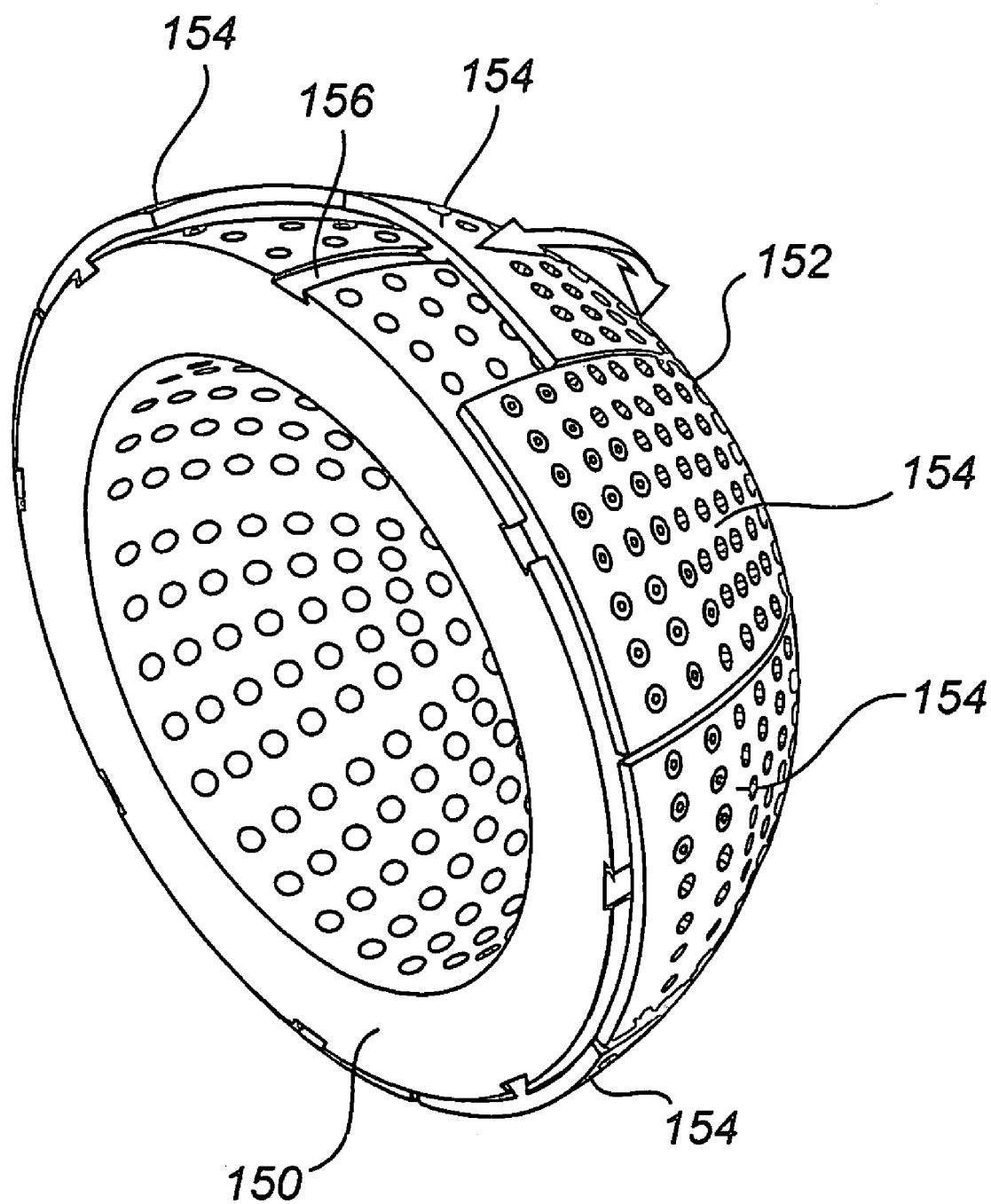
FIG. 17 is a perspective view of an assembly comprising a source carrier arrangement surrounding a collimator body, in accordance with a seventh embodiment of the invention.

FIG. 17 is a perspective view of an assembly comprising a collimator body 150 surrounded by a source carrier arrangement 152, in accordance with a seventh embodiment of the invention, which is similar to the embodiment shown in FIG. 15. In FIG. 16 the source carrier arrangement 152 essentially conforms with the outer shape of the collimator body 150. The source carrier arrangement 152 has eight individually controllable and displaceable segments 154. Each segment 154 may be brought to slide over the collimator body 150 by means of a trapezoidal thread, a groove 156 of which is provided in the collimator body 150 and a corresponding protrusion being provided on the segment 154. Each segment 154 is displaceable along the hemispherical collimator body from its base to its crest and vice versa, as indicated by the double-arrow.

Figure 18:
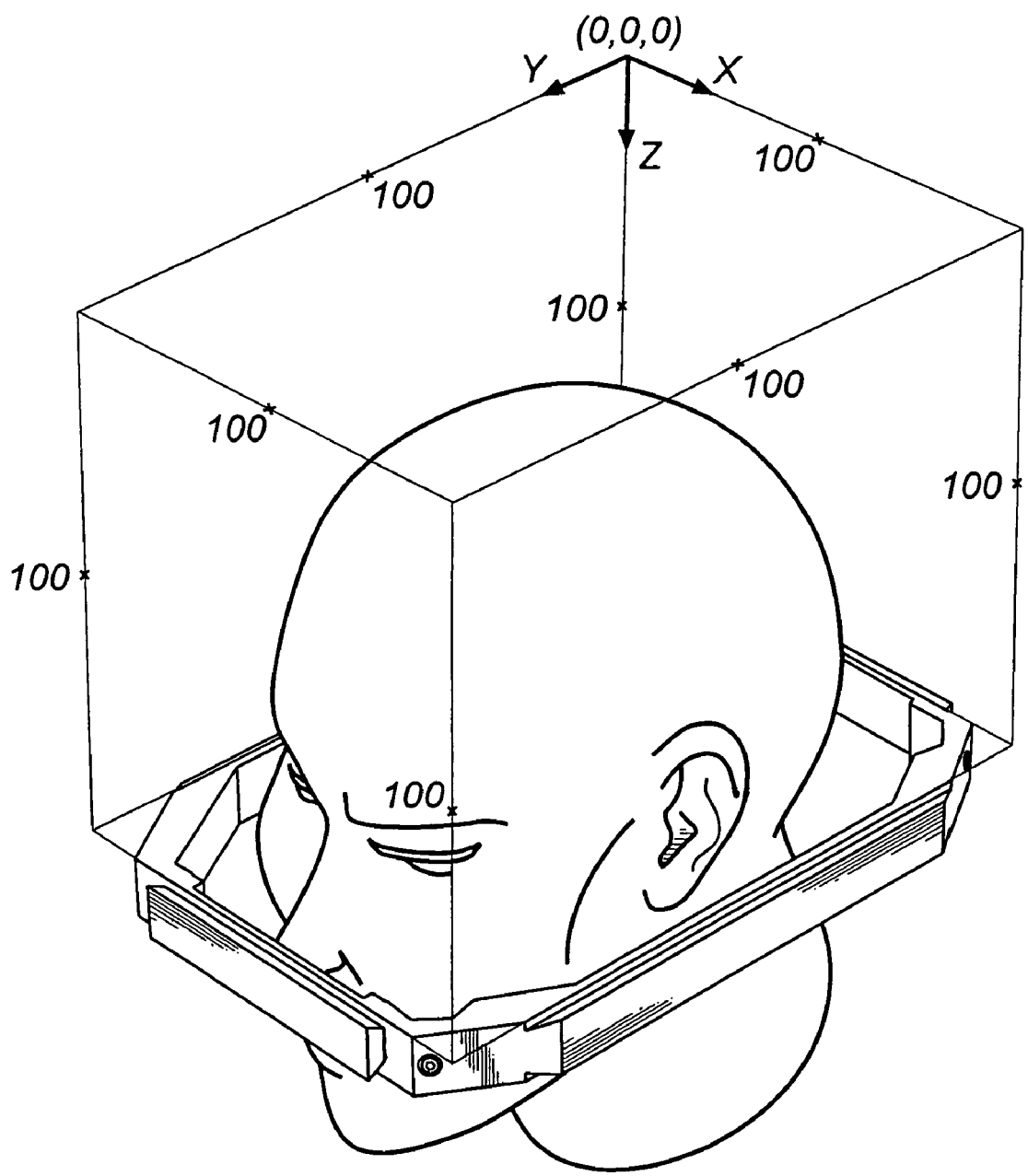
FIG. 18 illustrates the Leksell x-, y-, z-coordinate system.

FIG. 18 illustrates the Leksell x-, y-, z-coordinate system, which is a Cartesian coordinate system, in connection with a standard frame being applied around the patient's head. As can be seen in the figure the origin of coordinates (0, 0, 0) is located behind the back of the patient's head, outside the right ear and over the top of the patient's head. Thus, any target area or focus in the patient's head will be defined by positive coordinates. The x-axis extends in parallel to an imaginary line extending from the right ear to the left ear of the patient. The y-axis extends in parallel to a line drawn from the neck (posterior) to the nose (anterior) of the patient. The z-axis extends in parallel to the longitudinal direction of the patient's body.

What is claimed is:

1. A radiation therapy device, comprising:
a source carrier arrangement carrying radioactive sources; and
a collimator body comprising collimator passages for directing radiation emanating from said sources toward a substantially common focus, each collimator passage having an inlet for receiving said radiation;
wherein the source carrier arrangement surrounds the collimator body and is arranged to allow for a subset of said sources to be displaced relatively to said inlets, while the rest of said sources are fixed relatively to said inlets, thereby enabling a change of spatial dose distribution surrounding said focus.

2. The radiation therapy device as claimed in claim 1, wherein said source carrier arrangement comprises at least two segments, each segment carrying a subset of said sources and being individually displaceable.

3. The radiation therapy device as claimed in claim 2, wherein each segment is displaceable along an envelope surface of the collimator body.

4. The radiation therapy device as claimed in claim 2, wherein each segment is linearly displaceable relatively to the collimator body so as to cause the positions of said subset of sources to be linearly displaced relatively to the positions of at least a subset of collimator passage inlets.

5. The radiation therapy device as claimed in claim 2, wherein each segment comprises or is connected to a respective actuator, for controlling the displacement of the segment, wherein the direction of displacement is along the longitudinal axis of the actuator.

6. The radiation therapy device as claimed in claim 2, wherein each segment is displaceable along a curvature.

7. The radiation therapy device as claimed in claim 6, wherein the collimator body is of substantially hemispherical shape with an annular base, each segment being displaceable in a rotary motion in relation to an axis extending along the diameter of the annular base.

8. The radiation therapy device as claimed in claim 6, wherein the collimator body is of substantially hemispherical shape with an annular base, each segment being displaceable in a rotary motion in relation to an axis extending from the center of the annular base to the crest of the hemisphere.

9. The radiation therapy device as claimed in claim 6, wherein the collimator body has a cross-section of at least an arc of a circle, said sources and said collimator passage inlets being distributed along said arc of a circle, wherein each segment is displaceable along said arc of a circle or circumference of the circle.

10. The radiation therapy device as claimed in claim 2, wherein each segment is connected to at least one shaft, the segment being displaceable by rotating the shaft.

11. The radiation therapy device as claimed in claim 1, wherein each subset comprises at least one row of sources which are jointly placeable in register with collimator passage inlets aligned in a corresponding row, and which are jointly removable from said inlets, by displacement of a segment.

12. The radiation therapy device as claimed in claim 11, wherein said collimator body comprises several parallel rows of collimator passage inlets, at least one of said rows being associated with collimator passages that direct toward said focus radiation beams of a different cross-section than radiation beams directed by collimator passages associated with the other rows.

13. The radiation therapy device as claimed in claim 12, wherein said source carrier arrangement comprises at least two segments with each segment carrying a subset of said source and being individually displaceable, and wherein each segment is displaceable in a direction substantially perpendicular to and intersecting said rows of collimator passage inlets.

14. The radiation therapy device as claimed in claim 6, wherein said collimator body comprises:
a first set of rows of collimator passage inlets associated with collimator passages that provide radiation beams of a first cross-section;
a second set of rows of collimator passage inlets associated with collimator passages that provide radiation beams of a second cross-section; and preferably
at least a third set of rows of collimator passage inlets associated with collimator passages that provide radiation beams of a third cross-section;
wherein any row from one of said sets has, as its closest neighbour, a row from at least one of the other sets.

15. The radiation therapy device as claimed in claim 14, wherein said subset comprises a plurality of rows of sources which are arranged to be simultaneously placeable in register with collimator passage inlets from one of said sets, said plurality of rows of sources being simultaneously displaceable so that the sources of at least one of said rows of sources avoid being in register with collimator passage inlets.

16. The radiation therapy device as claimed in claim 1, wherein each one of said source carrier arrangement and said collimator body has a cross-section of at least an arc of a circle, said sources and said collimator passage inlets being distributed along said arc of a circle, wherein said subset of collimator passage inlets and said subset of sources are linearly displaceable relatively to each other in a direction substantially perpendicular to said cross-section.

17. The radiation therapy device as claimed in claim 1, wherein, in a Leksell x-,y-,z-coordinate system, said subset of collimator passage inlets and said subset of sources are linearly displaceable relatively to each other essentially in parallel to the z-axis.

18. The radiation therapy device as claimed in claim 1, wherein at least a portion of said source carrier arrangement has an envelope surface shaped substantially like a frustum of a cone.

19. The radiation therapy device as claimed in claim 18, wherein, in a Leksell x-,y-,z-coordinate system, said subset of sources are linearly displaceable at an angle of 0–45° to the z-axis.

20. A method of changing the spatial dose distribution surrounding a focus toward which collimator passages of a collimator body direct radiation emanating from radioactive sources carried by a source carrier arrangement of a radiation therapy device, each collimator passage having an inlet for receiving said radiation, and said source carrier arrangement surrounding said collimator body, comprising the step of:

displacing a subset of said sources relatively to said collimator passage inlets, while keeping the rest of the sources fixed relatively to said collimator passage inlets.

21. The method as claimed in claim 20, comprising displacing a first segment of the source carrier arrangement, while keeping at least another segment of the source carrier arrangement fixed, each segment carrying a subset of said sources.

22. The method as claimed in claim 21, comprising displacing said first segment along an envelope surface of the collimator body.

23. The method as claimed in claim 22, comprising displacing said first segment so that the sources are moved from a position in which they are in register with collimator passage inlets to a position in which they are not in register with collimator passage inlets.

24. The method as claimed in claim 22, comprising displacing said first segment so that the sources are moved from a position in which they are in register with inlets to coilimator passages of a first size to a position in which they are in register with inlets to collimator passages of a second size.

25. The method as claimed in claim 21, comprising displacing said first segment so that the sources are moved from a position in which they are in register with collimator passage inlets to a position in which they are not in register with collimator passage inlets.

26. The method as claimed in claim 21, comprising displacing said first segment so that the sources are moved from a position in which they are in register with inlets to collimator passages of a first size to a position in which they are in register with inlets to collimator passages of a second size.

27. The method as claimed in claim 21, comprising linearly displacing at least said first segment of said source carrier arrangement relatively to a collimator body having said collimator passages, thereby causing the positions of said subset of sources to be displaced relatively to at least a subset of collimator passage inlets.

28. The method as claimed in claim 21, comprising displacing said first segment essentially in parallel to the z-axis in a Leksell x-,y-,z-coordinate system.

29. The method as claimed in claim 20, comprising displacing said first segment in a direction having an angle of 0–45°, relatively to the z-axis in a Leksell x-,y-,z-coordinate system.

30. The method as claimed in claim 20, comprising displacing said first segment along a curvature.

* * * * *

UNITED STATES PATENT AND TRADEMARK OFFICE
CERTIFICATE OF CORRECTION

PATENT NO. : 6,968,036 B2
DATED : November 22, 2005
INVENTOR(S) : Per Carlsson et al.

It is certified that error appears in the above-identified patent and that said Letters Patent is hereby corrected as shown below:

<u>Column 14,</u>
Line 33, change "claim 6" to -- claim 13 --.

Signed and Sealed this

Twenty-fifth Day of April, 2006

JON W. DUDAS
*Director of the United States Patent and Trademark Office*